(12) United States Patent
Bantia

(10) Patent No.: US 9,616,129 B2
(45) Date of Patent: *Apr. 11, 2017

(54) COMPOSITIONS AND METHODS FOR POTENTIATING IMMUNE RESPONSE, ENHANCING IMMUNOTHERAPY, AND INCREASING VACCINE POTENCY

(71) Applicant: Nitor Therapeutics, Birmingham, AL (US)

(72) Inventor: Shanta Bantia, Birmingham, AL (US)

(73) Assignee: Nitor Therapeutics, Birmingham, AL (US)

(*) Notice: Subject to any disclaimer, the term of this patent is extended or adjusted under 35 U.S.C. 154(b) by 31 days.

This patent is subject to a terminal disclaimer.

(21) Appl. No.: 14/309,133

(22) Filed: Jun. 19, 2014

(65) Prior Publication Data

US 2014/0377250 A1    Dec. 25, 2014

Related U.S. Application Data

(60) Provisional application No. 61/838,252, filed on Jun. 22, 2013, provisional application No. 61/887,625, filed on Oct. 7, 2013, provisional application No. 61/934,094, filed on Jan. 31, 2014.

(51) Int. Cl.

| | | |
|---|---|---|
| *A61K 31/43* | (2006.01) | |
| *A61K 47/22* | (2006.01) | |
| *A61K 39/00* | (2006.01) | |
| *A61K 31/519* | (2006.01) | |
| *A61K 45/06* | (2006.01) | |
| *A61K 39/08* | (2006.01) | |
| *A61K 39/39* | (2006.01) | |
| *A61K 31/7064* | (2006.01) | |

(52) U.S. Cl.
CPC ............ *A61K 47/22* (2013.01); *A61K 31/519* (2013.01); *A61K 39/00* (2013.01); *A61K 39/08* (2013.01); *A61K 39/39* (2013.01); *A61K 45/06* (2013.01); *A61K 31/7064* (2013.01); *A61K 2039/55511* (2013.01)

(58) Field of Classification Search
None
See application file for complete search history.

(56) References Cited

U.S. PATENT DOCUMENTS

| | | |
|---|---|---|
| 4,938,949 A | 7/1990 | Borch et al. |
| 4,985,433 A | 1/1991 | Secrist, III et al. |
| 4,985,434 A | 1/1991 | Secrist, III et al. |
| 5,008,265 A | 4/1991 | Secrist, III et al. |
| 5,008,270 A | 4/1991 | Secrist, III et al. |
| 5,565,463 A | 10/1996 | Secrist, III et al. |
| 5,721,240 A | 2/1998 | Secrist, III et al. |
| 5,891,864 A | 4/1999 | Han et al. |
| 5,985,848 A | 11/1999 | Furneaux et al. |
| 6,066,722 A | 5/2000 | Furneaux et al. |
| 6,656,915 B1 | 12/2003 | Bantia et al. |
| 7,109,331 B2 | 9/2006 | Furneaux et al. |
| 7,390,890 B2 | 6/2008 | Furneaux et al. |
| 7,427,624 B2 | 9/2008 | Chen et al. |
| 7,553,839 B2 | 6/2009 | Evans et al. |
| 8,173,662 B2 | 5/2012 | Evans et al. |
| 8,283,345 B2 | 10/2012 | Evans et al. |
| 2001/0053784 A1 | 12/2001 | Morris, Jr. et al. |
| 2003/0114466 A1 | 6/2003 | Bantia et al. |
| 2005/0054590 A1 | 3/2005 | Averett |
| 2007/0082863 A1 | 4/2007 | Signorelli et al. |
| 2009/0239885 A1 | 9/2009 | Evans et al. |
| 2011/0038858 A1 | 2/2011 | Bantia et al. |
| 2011/0130412 A1 | 6/2011 | Clinch et al. |
| 2012/0114649 A1 | 5/2012 | Langermann et al. |

FOREIGN PATENT DOCUMENTS

| | | |
|---|---|---|
| EP | 2395005 | 12/2011 |
| WO | 2005025583 | 3/2005 |
| WO | 2008030119 | 3/2008 |

OTHER PUBLICATIONS

International Search Report and Written Opinion of PCT Application No. PCT/US2014/043141 mailed Oct. 10, 2014.

Bantia et al, "Potent orally bioavailable purine nucleoside phosphorylase inhibitor BCX-4208 induces apoptosis in B- and T-lymphocytes—a novel treatment approach for autoimmune diseases, organ transplantation and hematologic malignancies," Int Immunopharmacol Jul. 2010, vol. 10, No. 7, pp. 784-790.

Kicska et al, "Immucillin H, a powerful transition-state analog inhibitor of purine nucleoside phosphorylase, selectively inhibits human T lymphocytes," Proc Nat Acad Sci 10, Apr. 2001, vol. 98, No. 8, pp. 4593-4598.

Walker et al, "Purine nucleoside phosphorylase deficiency: a mutation update." Nucleosides, Nucleotides Nucleic Acids, Dec. 2011, vol. 30, No. 12, pp. 1243-1247.

International Search Report and Written Opinion for corresponding PCT Application No. PCT/US2014/43155 mailed Mar. 31, 2015.

*Primary Examiner* — Yong Chu
*Assistant Examiner* — Ana Z Muresan
(74) *Attorney, Agent, or Firm* — Dinsmore & Shohl LLP

(57) ABSTRACT

Compositions including at least one PNP inhibitor or at least one PNP inhibitor in combination with one or more agents identified as endogenous adjuvants useful for enhancing the potency of vaccine and cancer immunotherapies being administered for the prevention or treatment of infectious diseases or cancer. The compositions may be formulated as pharmaceutical dosage forms and components may be assembled as kits. Methods for increasing the levels of endogenous adjuvants to enhance the immunogenicity of an antigen as well as to augment the potency of vaccine and cancer immunotherapies are also disclosed.

10 Claims, 10 Drawing Sheets

COMPOSITIONS AND METHODS FOR POTENTIATING IMMUNE RESPONSE, ENHANCING IMMUNOTHERAPY, AND INCREASING VACCINE POTENCY

RELATED APPLICATIONS

This application claims the benefit of U.S. provisional application Ser. No. 61/838,252 filed on Jun. 22, 2013, U.S. provisional application Ser. No. 61/887,625 filed on Oct. 7, 2013, and U.S. Provisional Ser. No. 61/934,094 filed on Jan. 31, 2014 the entire disclosures of which are incorporated herein by this reference.

TECHNICAL FIELD

The technical field relates to pharmaceutical compositions comprising one or more Purine Nucleoside Phosphorylase (PNP) inhibitors and/or agents identified as endogenous adjuvants capable of providing an immune-potentiating effect in the presence of an antigen, vaccine or immunotherapy. The field also relates to methods for preventing and treating diseases, enhancing an immune response and augmenting the potency of vaccines and immunotherapies.

BACKGROUND

An adjuvant is an agent administered to potentiate an immune response to an antigen and/or to modulate an immune response toward a desired immune response. An endogenous adjuvant is a compound or molecule naturally occurring within a cell or tissue that likewise enhances an immune response by stimulating innate immunity, thus possessing the capacity to potentiate an effect of some triggering event or agent. Endogenous adjuvants play a central role in alerting the immune system to potential danger and in promoting response to infection, transplantation, tumor, and autoimmunity.

Vaccines attempt to safely elicit an immunity to pathogens that is ideally robust, protective and long-lived. However, current formulations of many subunit vaccines provide weaker and shorter-lived immunity than natural infection. While it is clear that adjuvants can be used to boost immunity, the adjuvants that are permitted in licensed vaccines are limited. Alum, a mixture of aluminum salts, was the first vaccine adjuvant that was widely utilized in vaccine preparations. It was the only vaccine adjuvant in use in the United States until 2009, when the U.S. Food and Drug Administration approved Cervarix, a human papillomavirus vaccine that contains an adjuvant designated as AS04. The AS04 adjuvant is a mixture of alum and a bacterial lipid (fat) molecule that has been modified so that it does not cause disease.

Alum, however, is a weak adjuvant and one that biases responses to effector responses (Th2) that are not protective against many pathogens. Endogenous adjuvants generally have not been evaluated for their potential use in vaccines. In theory, they may allow vaccinations to safely mimic the pathway that naturally triggers immunity to many pathogens. These agents also promote CD8+ T cell immune responses, which are important in immunity to many pathogens, such as viruses and tumors, but not elicited by most subunit vaccines (Rock et al. in *Springer Seminars in Immunopathology* (2005) 26:231-246).

Purine Nucleoside Phosphorylase (PNP) is an enzyme involved in purine metabolism. PNP metabolizes inosine and deoxyinosine into hypoxanthine, and guanosine and deoxyguanosine into guanine; in each case creating (deoxy) ribose phosphate. PNP-deficient patients exhibit significantly higher levels of plasma nucleosides including inosine, deoxyinosine, guanosine and deoxyguanosine when compared to PNP-normal subjects (Markert in *Immunodeficiency Review* (1991) 3:45-81), and further exhibit elevated levels of erythrocyte deoxyguanosine triphosphate (dGTP) and nicotinamide adenine dinucleotide (NAD). PNP-deficient patients inevitably manifest an immunodeficiency problem affecting T-cells and B-cells. Plasma deoxyguanosine (the only clinically measurable nucleoside) and intracellular dGTP are elevated in patients treated with PNP inhibitors (Bantia and Kilpatrick in *Current Opinions in Drug Discovery & Development* (2004) 7: 243-247). Deoxyguanosine was also elevated in mouse plasma after treatment with PNP inhibitor (Bantia et al. in *International Immuno-pharmacology* (2001) 1:1199-1210 and (2010) 10:784-790).

A major source of nucleoside pools comes from the breakdown of RNA and DNA during normal cell turnover, cellular injury or cell death due to infection. Normally the nucleosides deoxyguanosine, inosine, deoxyinosine, and guanosine are present at very low to undetectable levels in the plasma because PNP is an extremely efficient catalyst and rapidly breaks down inosine and deoxyinosine to hypoxanthine, and guanosine and deoxyguanosine to guanine and sugar 1-phosphate. In the presence of a PNP inhibitor or due to a PNP deficiency, however, these nucleosides become elevated. Guanosine analogs like isatoribine (7-thia, 8-oxoguanosine), loxoribine (7-allyl, 8-oxo guanosine) and others have been shown to be immuno-potentiators, demonstrating antiviral, antibacterial and anticancer effects in animal models (Smee et al. in *Antimicrobial Agents and Chemotherapy* (September 1989) 1487-1492; Stewart et al. in *J. Interferon Cytokine Research* (2012) 32(1):46-51; also in *Poult Science* (2012) 91(4):1038-1042; Pope et al. in *Cell Immunol.* (1995) 162(2):333-339).

ANA773, an oral pro-drug of isatoribine, has been demonstrated to induce endogenous interferon-a (IFN-a) of multiple subtypes in healthy volunteers. In clinical trials of chronically HCV infected patients, ANA773 demonstrated a dose-dependent reduction in HCV RNA (Bergmann et al. in *Aliment Pharmacol Ther* (2011) 34:443-453; International patent number WO2005025583A2).

In-vitro studies with guanosine analogs have shown activation of immune cells such as dendritic cells and natural killer cells to produce ifn-gamma, which is mediated through Toll-Like Receptor 7 (TLR7). Toll-like receptors (TLRs) have been established as a family of pathogen recognition receptors (PRR) that initiate the innate immune response. In addition to TLRs there are other PRR's, for example retinoic acid inducible gene I (RIGI) like receptors (RLR), nucleotide binding oligomerization domain (NOD)-like receptors (NLR) and c-type lectin receptors (CLR). Direct or indirect stimulation of TLRs and other PRRs causes the release of multiple cytokines including type 1 and type 2 interferons, the induction of pathways and enzymes that destroy intracellular pathogens, the activation of a variety of cellular responses, and the priming of the adaptive response by activation of immature dendritic cells, inducing their differentiation into professional antigen-presenting cells. At least eleven different TLR genes have been identified in humans. It appears that through stimulation of innate immunity by activating TLR, it is possible to prevent or reverse otherwise lethal viral infections in various acute infection models in mice.

Methyl inosine monophosphate, a particular inosine analog, has also shown immune enhancing effects and demonstrated antiviral and antibacterial effects (Mishin et al. in *Antiviral Research* (2006) 71:64-68).

In addition to the accumulation of nucleosides in the presence of PNP inhibitor, deoxyguanosine is converted to dGTP in lymphocytes and erythrocytes. dGTP could potentially stimulate the immune system through activation of PRR's in the presence of an antigen similar to what has been observed with ATP. Although the mechanism is not clear, PNP deficient patients also demonstrate increase in NAD levels. NAD may also serve as danger signal and activate the immune system (Haag et al., Purinergic Signalling (2007) 3: 71-81).

Based on the role of PNP in purine catabolism, the present investigators hypothesize that effective inhibition of PNP may elevate nucleosides, inosine, deoxyinosine, guanosine deoxyguanosine and nucleotides dGTP and NAD levels in a subject, as is seen in PNP-deficient patients and PNP-deficient mice (FIG. 1); however contrary to expectations based on the immuno-compromised clinical phenotype of the PNP-deficient patient, the present investigators have discovered that PNP inhibition in a PNP-normal patient results in an immune-potentiating effect.

There remains a need in the art for methods for preventing and treating diseases which exploit the natural endogenous adjuvant response. Controlling the levels of endogenous adjuvants provides a novel mechanism to exploit for enhancing immunogenicity of an antigen and augmenting potency of vaccines and cancer immunotherapies. Further, identification of endogenous adjuvants, triggered in response to certain pathogens, may provide novel exogenous adjuvants, which may thereafter be administered exogenously to enhance an immune response and augment the potency of vaccines and cancer immunotherapies.

SUMMARY OF DISCLOSURE

Accordingly, it is an object of the instant invention to provide compositions and methods which exploit the endogenous adjuvant response to enhance the immunogenicity of an antigen and to augment the potency of vaccines and cancer immunotherapies. The present disclosure provides articles of manufacture, methods and compositions effective for increasing levels of the nucleosides inosine, deoxyinosine, guanosine and deoxyguanosine, and for increasing levels of the nucleotides dGTP and NAD in a subject.

Compositions and methods for inhibiting PNP to effectuate an increase in inosine, deoxyinosine, guanosine, deoxyguanosine NAD and dGTP pools in a subject are described and detailed. These endogenous substances behave as endogenous adjuvants and can act as immune-enhancers in the presence of an antigen or vaccine and therefore act to enhance the potency of vaccine and immunotherapies, including specifically cancer immunotherapy. Such compositions and methods were not previously appreciated in the art.

Compositions, kits and methods useful for inhibiting PNP in combination with one or more exogenously administered agents that have been identified as endogenous adjuvants are also described. The agents include, for example, inosine, deoxyinosine, guanosine, deoxyguanosine, NAD and dGTP, individually or in any combination. The compositions act as immune-enhancers in the presence of an antigen or vaccine and act to enhance the potency of the vaccine and/or immunotherapy. Such compositions and methods were not previously appreciated in the art.

One embodiment provides methods of enhancing the potency of vaccine or cancer immunotherapies or the immunogenicity of an antigen by increasing an amount of at least one endogenous adjuvant, the method comprising administering a pharmaceutically effective amount of a purine nucleoside phosphorylase (PNP) inhibitor to a subject requiring treatment.

According to some embodiments, the methods may further comprise administering an agent identified as an endogenous adjuvant in conjunction with administration of the PNP inhibition. Administration "in conjunction with" may be at the same time, in the same treatment cycle or subsequent to administration of the PNP inhibitor.

Other embodiments are directed to methods for enhancing the potency of vaccine and cancer immunotherapies comprising administering a pharmaceutically effective amount of a composition comprising at least one purine nucleoside phosphorylase (PNP) inhibitor and at least one agent identified as an endogenous adjuvant to a subject requiring treatment.

According to other embodiments, compositions effective for enhancing the potency of vaccines and cancer immunotherapies in a subject are provided. The compositions comprise at least one PNP inhibitor and at least one agent identified as an endogenous adjuvant. Compositions may be formulated as oral dosage forms, parenteral dosage forms or topical dosage forms, and in specific embodiments the oral dosage form is formulated to provide delayed release of the PNP inhibitor relative to the agent identified as an endogenous adjuvant.

Kit embodiments are also disclosed. In some embodiments the kits comprise a first dosage form and a second dosage form, the first dosage form comprising a PNP inhibitor and the second dosage form comprising at least one agent identified as an endogenous adjuvant.

These and other embodiments and aspects of the present invention will be more fully understood and clarified by reference to the Detailed Description set forth below.

DETAILED DESCRIPTION

Figure 1:
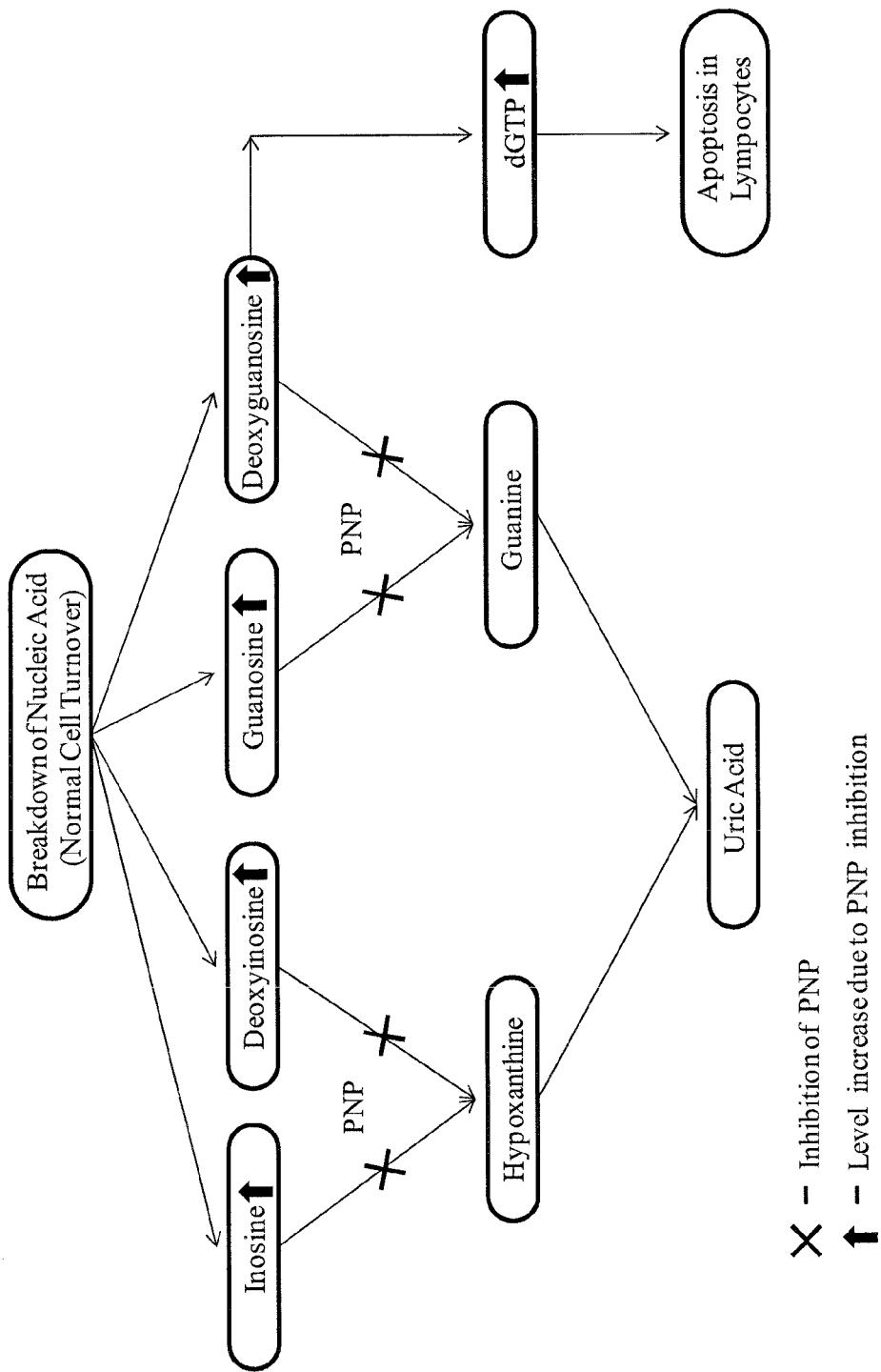
FIG. 1. Depicts a schematic illustration of the relationship between PNP inhibition and levels of inosine, deoxyinosine, guanosine, deoxyguanosine, and nucleotide dGTP levels.

New generation vaccines will increasingly comprise highly purified recombinant proteins. Unfortunately, these antigens are often poorly immunogenic. Therefore, adjuvants will be required to enable these proteins to become effective vaccines. Stimulation of the innate immune response is now known to have an important role in the evolution of the adaptive immune response. Hence, identification and inclusion of immune potentiators (also termed adjuvants), which trigger an early innate immune response to aid in the generation of robust and long lasting adaptive immune responses is crucial to vaccine effectiveness.

The instant disclosure provides compositions and methods effective for enhancing the potency of a vaccine or an immunotherapy administered to a subject as part of a prevention or treatment regimen. A broad embodiment is directed to a method comprising: administering a composition comprising a pharmaceutically effective amount of a purine nucleoside phosphorylase (PNP) inhibitor to a subject in conjunction with the vaccine or immunotherapy. The vaccine or immunotherapy may be for treatment or prevention of infectious disease or treatment or prevention of cancer. In specific embodiments the immunotherapy comprises administration of at least one indoleamine-pyrrole 2,3-dioxygenase (IDO1) inhibitor and/or one checkpoint modulator selected from the group consisting of CTLA-4 antagonists, GITR agonists, OX40 agonists, LAG-3 antagonists, TIM-3 antagonists and PD-1 antagonists, PDL-1 antagonists and CD-27 agonists. Very specific known drugs which act as checkpoint modulators include ipilimumab, lambrolizumab (anti-PD1), anti-programmed death ligand-1 (antiPD1-1), and CDX-1127. Immunotherapy by administration of one or more Toll-like Receptor agonists may also be potentiated by administration of a PNP-inhibitor. Examples of TLR agonists include TLR 2, TLR3, TLR4, TLR5, TLR7, TLR8, and TLR9 agonists.

TLRs play a critical role in the early innate immune response to invading pathogens by sensing microorganisms, and are also involved in sensing endogenous danger signals. TLRs recognize highly conserved structural motifs known as pathogen-associated microbial patterns (PAMPs), which are exclusively expressed by microbial pathogens, and/or danger-associated molecular patterns (DAMPs) that are endogenous molecules released from necrotic or dying cells. Stimulation of TLRs by the corresponding PAMPs or DAMPs initiates signaling cascades leading to the activation of transcription factors, such as AP-1, NF-κB and interferon regulatory factors (IRFs). Signaling by TLRs results in a variety of cellular responses including the production of interferons (IFNs), release of pro-inflammatory cytokines and release of effector cytokines that direct the adaptive immune response.

PNP (sometimes referred to as PNPase) deficiency is known to result in an increase in levels of the substrates of the enzyme. Non-limiting examples of PNP substrates include inosine, deoxyguanosine, deoxyinosine and guanosine. In addition to increases in specific nucleosides, PNP inhibition also leads to accumulation of intracellular dGTP and NAD (Markert in *Immunodeficiency Review* (1991) 3:45-81). The present investigators posit that these nucleosides as well as nucleotides dGTP and NAD can act as endogenous adjuvants similar to other purines known as putative endogenous adjuvants, such as uric acid, ATP and adenosine. These endogenous adjuvants can then activate the immune system through TLRs and/or other PRRs in the presence of an appropriate antigen/vaccine or cancer immunotherapy.

FIG. 1 is a schematic presentation of the role of PNP in purine metabolism which illustrates the relationship between PNP inhibition and observed increases in inosine, deoxyinosine, guanosine, deoxyguanosine, and dGTP levels.

PNP-deficiency is an extremely rare autosomal recessive metabolic disorder which results in severe combined immunodeficiency and a profile of symptoms associated with immunodeficiency, such as depletion of T-cells, decline of lymphocyte activity, and an abrupt proliferation of both benign and opportunistic infections. Due to the rarity of the condition, investigators have developed a knock-out mouse model. PNP-deficient patients and PNP-deficient mice exhibit high levels of the PNP-substrate nucleosides as well as nucleotides NAD and dGTP. Patients treated with PNP inhibitor or animals treated with PNP inhibitor also show increases in plasma levels of deoxyguanosine. A major source of nucleoside pools comes from the breakdown of RNA and DNA during cellular injury or cell death. Normally, the nucleosides deoxyguanosine, inosine, deoxyinosine, and guanosine are present at very low or undetectable levels in the plasma because PNP rapidly breaks down inosine and deoxyinosine to hypoxanthine, and breaks down guanosine and deoxyguanosine to guanine and sugar 1-phosphate. In the presence of PNP inhibitor or PNP deficiency these nucleosides are elevated. In contrast with what might be expected based on the immuno-deficient profile of the PNP-deficient patient, the present investigators discovered that these nucleosides could potentially act as endogenous adjuvant and actually activate the immune system. Without wishing to be bound by theory, increases in one or more of these PNP substrates due to inhibition of PNP could act as a danger signal (endogenous adjuvant) and enhance the immune system in the presence of an antigen. PNP inhibitors could potentially be used as immune-response enhancers by functioning as adjuvants in vaccine and cancer immunotherapies targeting the prevention and treatment of infectious diseases and cancer. In some embodiments the inventive compositions may further comprise at least one agent identified as an endogenous adjuvant.

Guanosine analogs such as isatoribine (7-thia, 8-oxoguanosine) and loxorabine (7-allyl, 8-oxo guanosine) have demonstrated immune-potentiating effects. In-vitro studies with some guanosine analogs have shown activation of immune cells, for example dendritic cells and natural killer cells to produce ifn-gamma which is mediated through Toll-Like Receptor 7 (TLR7).

Through stimulation of innate immunity by activating TLR, administration of isatoribine and other guanosine analogs appears to prevent or reverse otherwise lethal viral infections in various acute infection models in mice. The present investigators therefore posit that by inhibiting PNP, guanosine and other nucleoside levels are elevated, which may activate an innate immune response through TLRs and other PRRs similar to activation by the guanosine analogs isatoribine and loxoribine.

Embodiments of the present invention therefore provide methods for preventing and treating diseases which recognize and exploit the natural endogenous adjuvant response. Controlling/modulating the levels of endogenous adjuvants provides a novel means to enhance immunogenicity of an antigen and augment potency of vaccines and cancer immunotherapies. Further, identification of endogenous adjuvants triggered in response to certain pathogens could provide novel exogenous adjuvants which may be administered in conjunction with vaccine and immunotherapy to enhance an immune response and augment potency.

Aspects of the invention related to affirmatively inhibiting PNP to effectuate elevation of plasma inosine, deoxyinosine, guanosine, and deoxyguanosine levels and intracellular NAD and dGTP levels in a subject, as is observed in PNP deficient patients (FIG. 1).

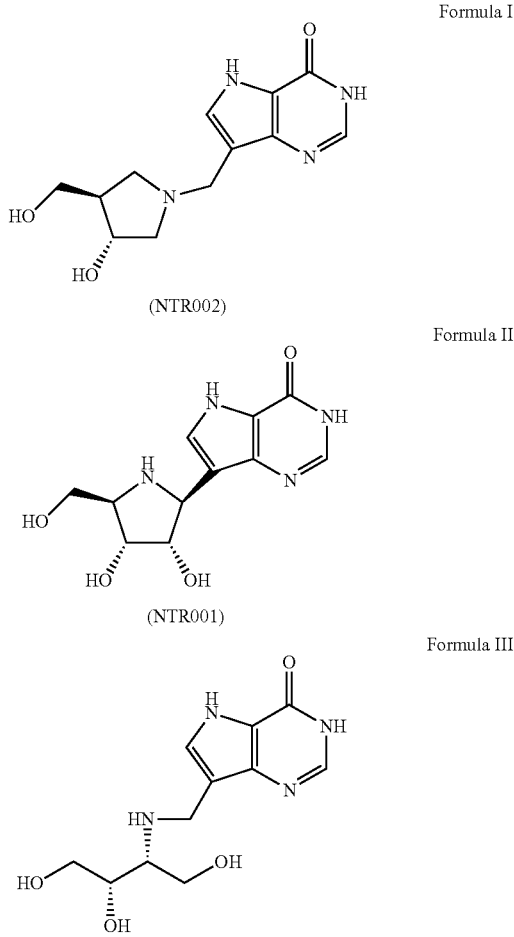

Compounds depicted structurally by Formula I (NTR002, also known as Ulodesine 1,5-dihydro-7-[[(3R,4R)-3-hydroxy-4-(hydroxymethyl)pyrrolidin-1-yl]methyl]-4H-pyrrolo[3,2-d]pyrimidin-4-one), Formula II (NTR001, also known as Forodesine 7-[(2S,3S,4R,5R)-3,4-dihydroxy-5-(hydroxymethyl)-2-pyrrolidinyl]-1,5-dihydro-4H-pyrrolo[3,2-d]pyrimidin-4-one) and Formula III have been shown to inhibit PNP. Further, structurally similar compounds known as transition state analogs have been studied as PNP inhibitors (Evans et al. in Organic Letters (2003) 5:3639; Taylor et al. in *Journal of American Chemical Society* (2007) 129:6984; Evans et al. in *Journal of Medicinal Chemistry* (2003) 46:5271; Castilho et al. in *Bioorganic & Medicinal Chemistry* (2006) 14:516; Schramm et al. in *Journal of Biological Chemistry* (2007) 282:28297; and Bantia et al. in *International Immunopharmacology* (2010) 784 and (2001) 1:1199-1210; Kicska et al. in *Proceedings of National Academy of Sciences* (2001) 98:4593-4598). The disclosures of each of these references are hereby incorporated in the entirety by this citation. Non-limiting examples of PNP inhibitors include those disclosed in U.S. Pat. Nos. 4,985,433; 4,985,434, 5,008,265; 5,008,270; 5,565,463 7,427,624, 5,721,240, 5,985,848, 7,390,890 and the continuation patents that are referenced therein, U.S. Pat. Nos. 7,109,331, 8,283,345, 8,173,662 and 7,553,839, and International Patent Number WO2008/030119 and EP2395005, the disclosures of which are also incorporated herein in the entirety by this reference.

The term "PNP inhibitor" includes compounds/molecules that inhibit PNP by any direct or indirect mechanism. It is entirely predictable that any agent shown to be a PNP inhibitor will be effective in the present methods; however in specific embodiment an effective PNP inhibitor comprises a transition state analog of PNP having an in-vitro inhibitory constant Ki value of less than about $5\times10^{-6}$ M. Compositions having in-vitro inhibitory constant (Ki) values of less than about $5\times10^{-6}$ M, typically less than about $1\times10^{-7}$ M, and preferably less than $5\times10^{-8}$ M are preferred for in vivo use. One embodiment relates to the use of PNP inhibitors as immune-potentiators in the presence of an antigen.

In another embodiment, methods and compositions for inhibition of PNP to effectuate increases in the level of one or more of inosine, deoxyinosine, guanosine, deoxyguanosine, NAD and dGTP are provided. Yet another embodiment is directed to enhancing the potency of vaccines and immunotherapies. In certain aspects, the potency of vaccines and immunotherapies for the prevention and treatment of infectious diseases and cancer may be enhanced by effectuating an elevation in inosine, deoxyinosine, guanosine, deoxyguanosine, NAD and/or dGTP levels, each of which individually or in combination can act as an endogenous adjuvant effective for stimulating the immune system.

In other embodiments, the present disclosure provides compositions comprising at least one agent identified as an endogenous adjuvant. According to one aspect, an agent may be identified as an endogenous adjuvant if endogenous levels of the agent in a subject increase in response to administration of a PNP inhibitor to the subject. In some aspects the increase is associated with an immune-response stimulating effect. In another embodiment, the compositions may additionally comprise one or more PNP inhibitors. In a specific embodiment the agent is selected from inosine, deoxyinosine, guanosine, deoxyguanosine, NAD, dGTP and combinations thereof. Methods effective for enhancing potency of vaccines and immunotherapy comprising administration of the compositions according to the invention are also provided.

The present disclosure also provides articles of manufacture for increasing nucleoside levels in a subject. According to specific embodiments the nucleosides are selected from the group consisting of inosine, deoxyinosine, guanosine, deoxyguanosine, and combinations thereof. Articles of manufacture for increasing nucleotides NAD and/or dGTP levels in a subject are also provided. In some aspects, articles of manufacture enhance the potency of vaccines and cancer immunotherapies related to increases in nucleosides, inosine, deoxyinosine, guanosine, and deoxyguanosine, and nucleotides NAD and dGTP levels. The article of manufacture comprises at least one reservoir containing a composition comprising one or more of compounds structurally depicted by formula I, II, and III, trivial variants thereof, PNP inhibitors listed in U.S. Pat. Nos. 5,985,848, 6,066,722 and 7,553,839, and International Patent Number WO2008/

030119, and agents identified as an endogenous adjuvant including but not limited to inosine, deoxyinosine, guanosine, deoxyguanosine, NAD and dGTP. The articles of manufacture may be packaged with indications for various disorders that the compositions are contemplated to treat. For example, the articles of manufacture may comprise a unit dose of a composition according to the invention, and an indication that the unit dose is capable of treating a certain disorder.

Compounds of formula I, II and III are 9-deazahypoxanthine derivatives. Specifically the compound of formula I is known in the art as Ulodesine and may be referred to herein as NTR002. The compound of formula II is known in the art as Forodesine and may be referred to herein as NTR001. Compounds of formula I, II, III and related compounds are described in U.S. Pat. Nos. 5,985,848, 6,066,722, and 7,553,839 and International Patent Number WO2008/030119. In some embodiments of this disclosure, these compounds can exist as a pharmaceutically acceptable salt. In other embodiments these compounds can exist as a tautomer. In yet other embodiments these compounds can exist as a solvate. In additional embodiments these compounds can exist as a hydrate. According to other embodiments these compounds can exist as a prodrug.

According to embodiments comprising administration of at least one agent identified as an endogenous adjuvant in conjunction with administration of the PNP inhibitor, the agent identified as an endogenous adjuvant is selected from the group consisting of guanosine, inosine, deoxyinosine, deoxyguanosine, nicotinamide adenine dinucleotide, deoxyguanosine triphosphate, pro-drugs thereof, and combinations thereof. In very specific embodiments the agent is guanosine or a pro-drug thereof. Analogs of guanosine with retention of efficacy are also contemplated as within the scope of the invention.

Administration may be via an enteral or parenteral or topical route or any other known method of administration in the literatures. In very specific embodiments administration may be oral. Administration "in conjunction with" according to the present invention may mean simultaneous as part of the same composition, or it may mean simultaneous in two distinct dosage forms, or in some embodiments it may mean in tandem separated by seconds, minutes, hours or days. In specific embodiments the agent identified as an endogenous adjuvant will be administered after the PNP inhibitor. In very specific embodiments PNP inhibitor will be administered one hour or more after the agent identified as an endogenous adjuvant. All these exemplary embodiments fall within the scope of "in conjunction with."

According to some aspects, an oral, parenteral or topical dosage form of the compositions of PNP-inhibitor and endogenous adjuvant are formulated to provide delayed release of the PNP inhibitor relative to release of the endogenous adjuvant. For example, the PNP-inhibitor may be integrated into a delayed release matrix while the endogenous adjuvant may be layered over the delayed release matrix. Such delayed release forms are well known in the art (see Allen and Ansel, "Ansel's Pharmaceutical Dosage Forms and Drug Delivery Systems" $10^{th}$ Edition, 2014 Lippincott, Williams and Wiklins, the entire contents of which is incorporated herein by this reference).

In the alternative, kits may be provided comprising a first dosage form and a second dosage form, the first dosage form comprising a PNP inhibitor and the second dosage form comprising at least one agent identified as an endogenous adjuvant.

Furthermore, in the embodiments described above, the article of manufacture may contain a therapeutically effective amount of one or more of compounds of formula I, II, III and related compounds described in U.S. Pat. Nos. 5,985,848, 6,066,722 and 7,553,839 and International Patent Number WO2008/030119, and one or a combination of inosine, deoxyinosine, guanosine, deoxyguanosine, and dGTP.

In some embodiments described above, the article of manufacture may further comprise, consist essentially of or consist of one or more additional active agents in combination with compounds of formula I, II, III and related compounds described in U.S. Pat. Nos. 5,985,848, 6,066,722 and 7,553,839, and International Patent Number WO2008/030119, and optionally one or a combination of inosine, deoxyinosine, guanosine, deoxyguanosine, NAD and dGTP.

In some embodiments described above, the article of manufacture may further comprise, consist essentially of or consist of one or more additional active agents in combination with compounds of formula I, II, III and related compounds described in U.S. Pat. Nos. 5,985,848, 6,066,722 and 7,553,839, and International Patent Number WO2008/030119, Examples of other active agents include, but are not limited to, analgesic agents, anti-inflammatory agents, anti-infective agents, chemotherapeutic agents, other immune enhancers or immunotherapies and agents that inhibit purine metabolism or other active agents know in the art.

The present disclosure provides methods for increasing inosine, deoxyinosine, guanosine deoxyguanosine, NAD and dGTP levels in a subject receiving a vaccine or cancer immunotherapy. In certain embodiments it is important that the dosing schedule of the PNP inhibitor be structured to avoid significantly impacting lymphocytes in the subject. According to this embodiment, a "significant impact" occurs when the patient exhibits symptoms associated with a reduction in lymphocytes not due to any underlying disease condition. According to specific embodiments, the patient is contemplated for immunotherapy for the treatment of cancer, and in very specific embodiments the cancer is a non hematologic cancer.

The present disclosure further provides methods for increasing inosine, deoxyinosine, guanosine deoxyguanosine, NAD and dGTP levels in a subject receiving vaccine or cancer immunotherapy, the method comprising administering to the subject a therapeutically effective amount of one or more compounds of the formula I, II and III, a trivial variant thereof, or a pharmaceutically acceptable salt, tautomer, isomer, prodrug, solvate or hydrate thereof and an optional pharmaceutically acceptable carrier.

In another embodiment, the present disclosure provides for methods for enhancing the immune response in a subject receiving vaccine or cancer immunotherapy, the method comprising administering to the subject a therapeutically effective amount of compound of the formula I, II and III or a pharmaceutically acceptable salt, tautomer, isomer, prodrug, solvate or a hydrate thereof, one or combination of the four nucleosides inosine, deoxyinosine, guanosine and deoxyguanosine, and nucleotides NAD and dGTP and an optional pharmaceutically acceptable carrier.

In one embodiment, effective dosages of the compounds of the invention can be determined by comparing their in vitro activity to their respective in vivo activity in animal models. Methods for the extrapolation of effective dosages in mice and other animals to humans are known to the art; for example, as described in U.S. Pat. No. 4,938,949, the entire disclosure of which is incorporated herein by reference.

It is known that PNP inhibition in humans over long term at certain doses leads to decreases in various lymphocyte subsets (Gomes et al. in Blood ASH Annual Meeting Abstracts (2008) 112: Abstract 2583). Hence, long term treatment with high doses of PNP inhibitor may have immunosuppressive effects. Surprisingly, the present investigators discovered that PNP inhibitors exhibit an immune-potentiating effect in the presence of an antigen if doses are selected to avoid significant impact on lymphocytes.

The following Examples are set forth to illustrate certain aspects and features of the instant inventive subject matter and should not be construed as limiting the full scope as defined by the claims appended hereto. Example 1 described below demonstrate that guanosine, which is one of the nucleoside that is elevated when PNP is inhibited, activate TLR2 and TLR4. Activation of TLR2 and TLR4 results in immune potentiating effects as it leads to expression of transcription factors (like NF-kB and IRF-3) resulting in expression of inflammatory cytokines and other cellular activation events. Examples 2, 3 and 4 demonstrate the immune potentiating activity of PNP inhibitor in various in-vivo mouse models. For purposes of interpreting this disclosure, Formulas I, II and III include trivial variants thereof, the term "trivial" being with respect to pharmaceutical efficacy. NTR001 is depicted structurally as Formula II, and NTR002 is depicted structurally as Formula I.

EXAMPLE 1

Toll-Like Receptor (TLR) Ligand Screening:
In-Vitro Activity of the PNP Inhibitor (PNPi),
Guanosine and Inosine on Seven Different Human
TLRs (TLR2, 3, 4, 5, 7, 8 and 9) as a Potential
Agonist Background:
TLRs play a critical role in the early innate immune response to invading pathogens by sensing microorganism and are involved in sensing endogenous danger signals. TLRs recognize highly conserved structural motifs known as pathogen-associated microbial patterns (PAMPs), which are exclusively expressed by microbial pathogens, or danger-associated molecular patterns (DAMPs) that are endogenous molecules released from necrotic or dying cells. Stimulation of TLRs by the corresponding PAMPs or DAMPs initiates signaling cascades leading to the activation of transcription factors, such as AP-1, NF-κB and interferon regulatory factors (IRFs). Signaling by TLRs result in a variety of cellular responses including the production of interferons (IFNs), pro-inflammatory cytokines and effector cytokines that direct the adaptive immune response.

Objective:
The objective of this study is to determine the activity of NTR001 (Forodesine set forth as Formula II), inosine and guanosine as single agents and in combination on seven different human TLRs (TLR2, 3, 4, 5, 7, 8 and 9) as a potential agonist.

Method:
TLR stimulation is tested by assessing NF-κB activation in HEK293 cells expressing a given TLR. The Secreted Embryonic Alkaline Phosphatase (SEAP) reporter is under the control of a promoter inducible by the transcription factor NF-κB. This reporter gene allows the monitoring of signaling through the TLR, based on the activation of NF-κB. The compounds are evaluated at one concentration and compared to control ligands. This step is performed in triplicate.

Figure 2:
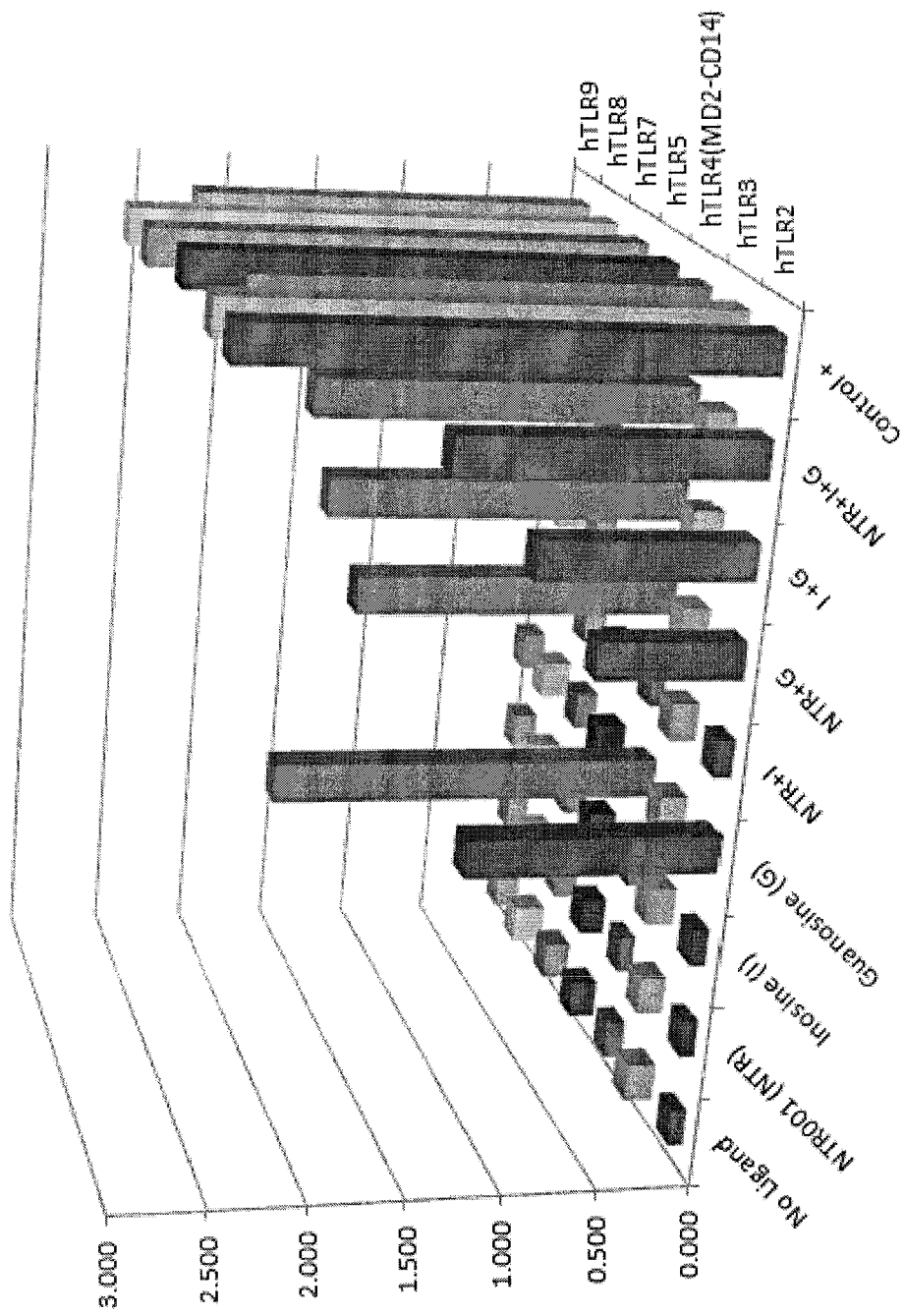
FIG. 2. Sets forth data demonstrating activity of the NTR001, inosine and guanosine as single agents and in combinations on seven different human TLRs (TLR2, 3, 4, 5, 7, 8 and 9) as potential agonists.

Results:
Guanosine (100 uM) exhibits a significant stimulatory effect on human TLR2 and TLR4, alone or in combination with article NTR001 (10 uM) and/or Inosine (100 uM). NTR001, Inosine, and NTR001+Inosine do not exhibit a stimulatory effect on human TLR2, 3, 4, 5, 7, 8 or 9 (FIG. 2).

Conclusion:
Guanosine is an agonist of TLR2 and TLR4 receptors. Activation of TLR2 and TLR4 results in immune activation and hence guanosine in the presence of PNPi (to prevent breakdown of guanosine) or PNPi alone (elevates guanosine in vivo) would be beneficial as vaccine adjuvants or to enhance potency of immunotherapies for the prevention and the treatment of cancer and infections.

EXAMPLE 2

Evaluation of PNPi as an Adjuvant in Tetanus
Toxoid Vaccine Efficacy Study

Background:
Aluminium based mineral salts (Alum) have been used as adjuvants in licensed vaccines for many years. Although alum has been shown to be safe and effective in traditional vaccines where eliciting antibody response is necessary, it is a weak adjuvant for protein subunits, which is one of the major drawbacks. Another limitation of alum is that it fails to induce the Th1 response associated with the induction of interferon-gamma (interferon-g) and cytotoxic T lymphocytes (CTL). Natural control of infectious diseases such as HIV, malaria and tuberculosis that cause the most global mortality are either entirely or partially dependent on the generation of Th1-type immunity. Hence, there is sufficient interest to develop new vaccine adjuvants. PNP inhibitors are novel small molecule that can potentially act as an adjuvant.

Objective:
One objective of this study is to investigate whether the PNP inhibitors NTR001 (Forodesine set forth structurally herein as Formula II) and NTR002 (Ulodesine set forth structurally herein as Formula I) enhance the potency of the tetanus toxoid vaccine by increasing the antibody titers. Another objective is to investigate whether the PNP inhibitors can induce Th1 responses associated with the induction of interferon-g.

Method:
Tetanus toxoid (TT) was used to vaccinate mice thrice, two weeks apart. Mice were treated by oral administration of compounds NTR001 and NTR002 and serum was collected at various time points for antibody titer and interferon-g analysis. Mice in Groups 2-6 (Table 2) are vaccinated subcutaneously with 0.1 ml tetanus toxoid vaccine on DAYS 0, 14 and 28. Mice in Group 1 (Table 1) received no vaccine. Treatments are done as shown in Table 1. Antibody titers for DAYS 38 are determined by ELISA using tetanus toxoid coated microtiter plates and anti-mouse conjugate. Sera from DAY 30 are assayed by ELISA for interferon-g.

TABLE 1

Group Compound Treatments

| Group | No. Mice | Test Material | ROA | Dose | Dose Frequency |
|---|---|---|---|---|---|
| 1 | 6 | Vehicle | p.o.* | N/A | Days 0, 14, 28 no vaccine |
| 2 | 6 | Vehicle | p.o. | N/A | Days 0, 14, 28 vaccinated |
| 3 | 6 | NTR001 | p.o. | 30 | Days 0, 1, 14, 15, 28, 29 |

TABLE 1-continued

Group Compound Treatments

| Group | No. Mice | Test Material | ROA | Dose | Dose Frequency |
|---|---|---|---|---|---|
| 4 | 6 | NTR001 | p.o. | 60 | Days 0, 14, 28 |
| 5 | 6 | NTR002 | p.o. | 30 | Days 0, 1, 14, 15, 28, 29 |
| 6 | 6 | NTR002 | p.o. | 60 | Days 0, 14, 28 |

*p.o. = oral dose

Figure 3:
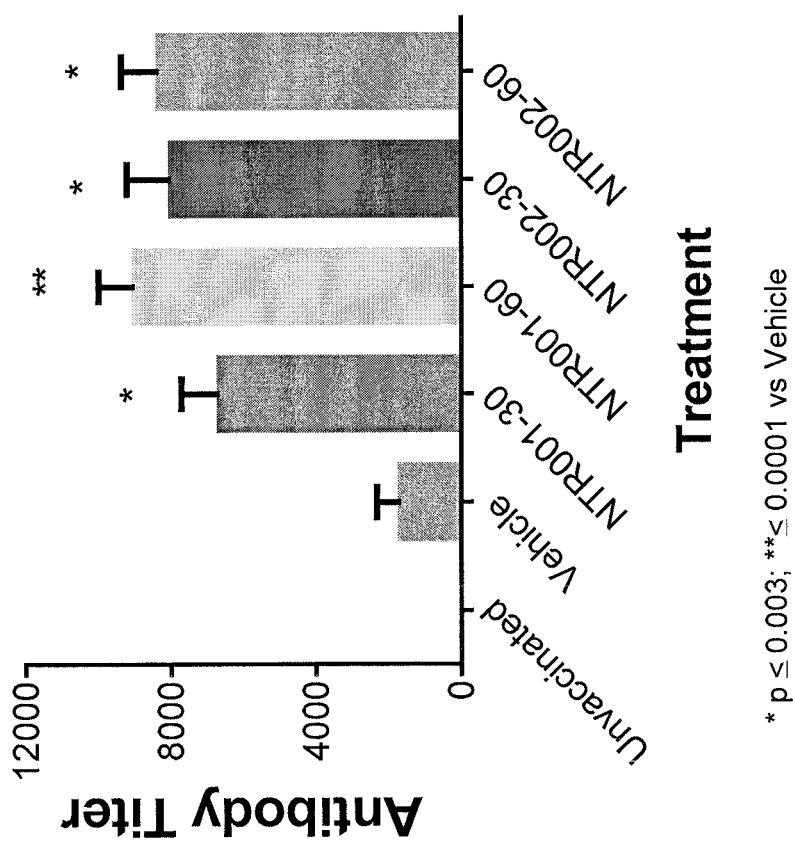
FIG. 3. Shows serum tetanus toxoid antibody titers on day 38 in control, NTR001- and NTR002-treated mice groups in the tetanus toxoid mouse model.
Figure 4:
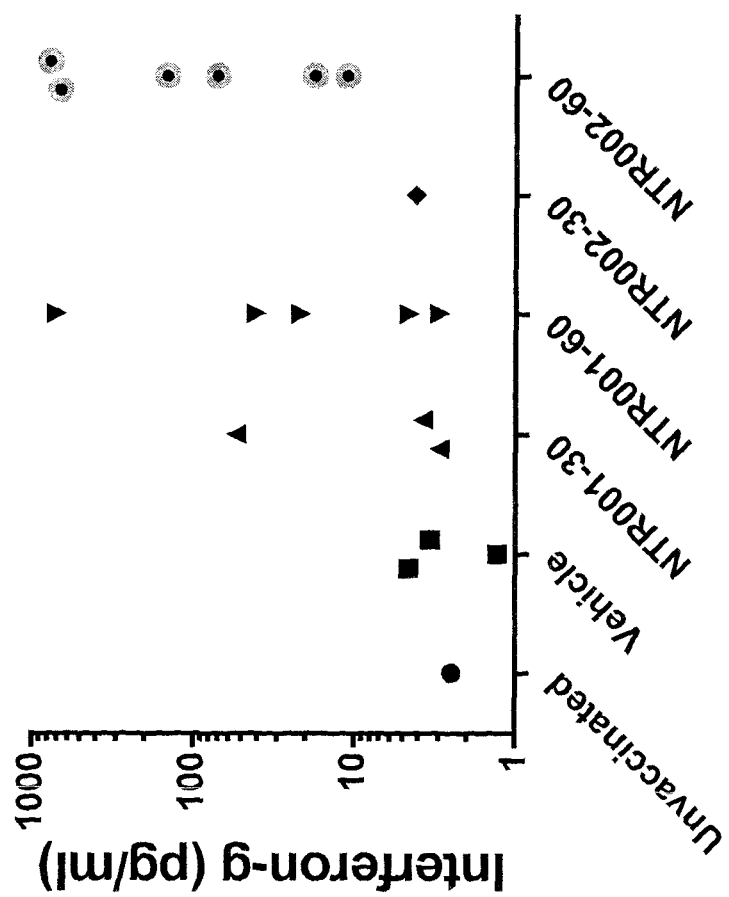
FIG. 4. Shows serum interferon-g levels on day 30 in control and NTR001- and NTR002-treated mice groups in the tetanus toxoid mouse model.

Results:

Both NTR001 and NTR002 PNP inhibitors significantly elevated the tetanus toxoid antibody titers compared to the vehicle treated group. The two dosing regimens, 30 mg/kg (given on the day of vaccination and the following day with a total of 6 days of treatment) and 60 mg/kg (given on the day of the vaccination with a total of 3 days of treatment), were effective in increasing the antibody titers (FIG. 3). The interferon-g was elevated in the high dose group (60 mg/kg) for both PNP inhibitors compared to the vehicle treated group (FIG. 4).

Conclusion:

PNP inhibitors NTR001 and NTR002 enhanced the potency of the tetanus toxoid vaccine by increasing the antibody titers and importantly, the PNP inhibitors induced Th1 responses associated with the induction of interferon-g. Thus, the PNP inhibitors represent a novel approach to enhancing both cellular and humoral immunity and may be useful as a vaccine adjuvant.

EXAMPLE 3

Evaluation of PNPi as Anticancer Agent in Mouse Melanoma Model

Background:

Chemotherapy is used to treat diverse cancers, but chemotherapy alone is insufficient to cure many advanced cancers, owing to side effects and the limited efficacy against chemo-resistant or relapsing tumors. The need for establishing more efficacious anticancer strategies led to the development of immunotherapies. PNP inhibitors are novel small molecule immune-potentiating agents that may demonstrate benefit in cancer treatment.

Objective:

The objective of this study is to investigate whether PNP inhibitor, a small molecule immune enhancer, demonstrates efficacy in reducing tumor volume and/or increasing survival in a syngeneic mouse model of B16 tumors in C57BL/6 mice.

Method:

Cancer cells were injected subcutaneously in right flank of each mouse, $1\times10^4$ cells in 0.1 ml PBS with 20% Matrigel. Treatment with the NTR001 was initiated on day 6 after injection of tumor cells. Tumor volume and survival were recorded every 3-4 days. Treatment arms were as follows:

TABLE 2

GROUP TREATMENTS

| Group | No. Mice | Material | Dose (mg/kg) | ROA | Frequency |
|---|---|---|---|---|---|
| 1 | 10 | Vehicle | 0 | PO | 4 wks (week on/off)* |
| 2 | 10 | NTR001 | 30 | PO | 4 wks (week on/off) |
| 3 | 10 | Cyclophosphamide | 100 | IP | Single Dose |
| 4 | 10 | Cyclophosphamide and NTR001 | 100 30 | IP PO | Single Dose 4 wks (week on/off) |
| 5 | 10 | NTR001 | 5 | Drinking water | 28 days |
| 6 | 10 | Cyclophosphamide NTR001 | 100 5 | IP Drinking water | Single dose 28 days |

*one week on treatment one week off treatment

Figure 5:
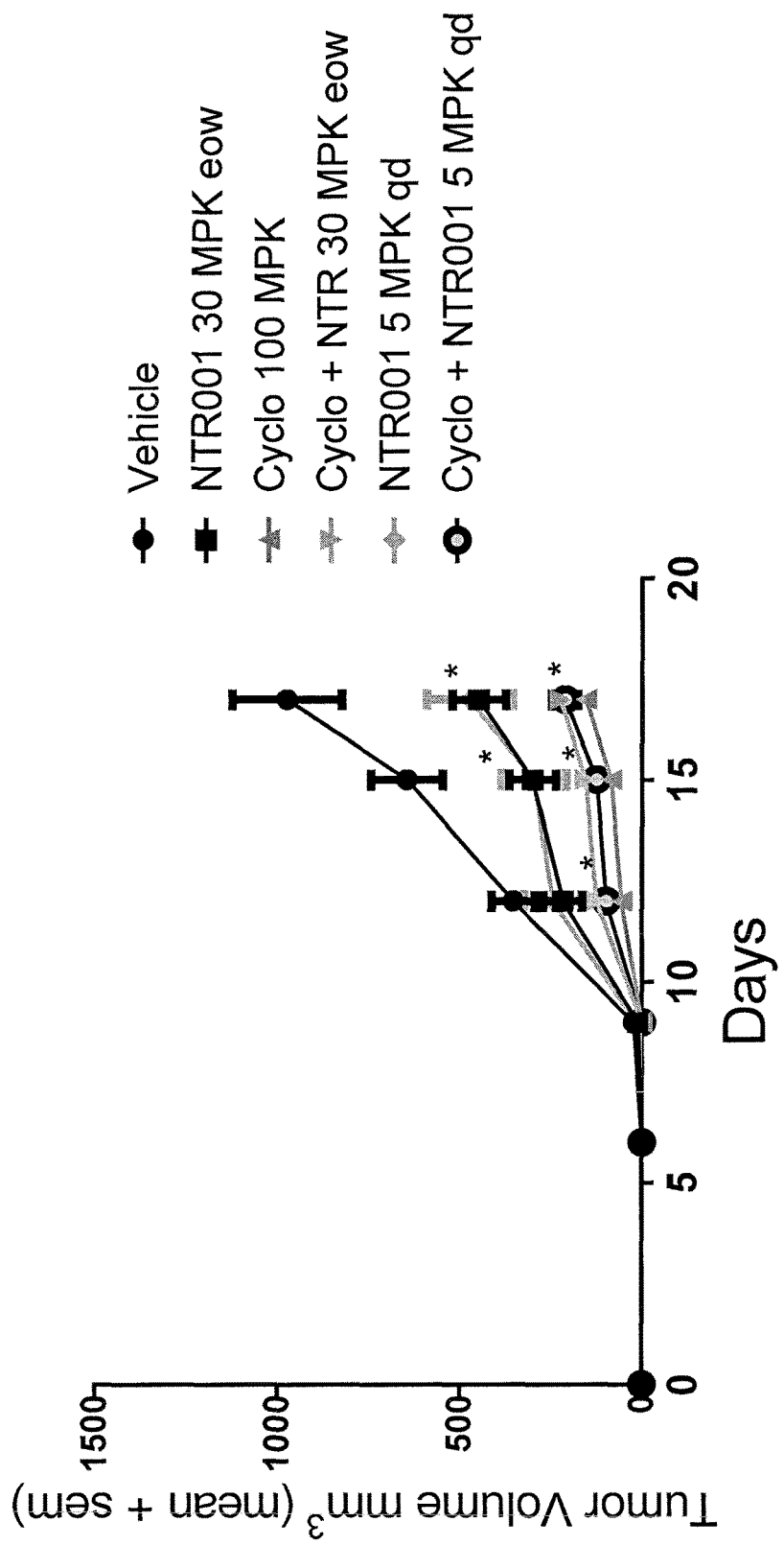
FIG. 5. Illustrates effect of PNP inhibitor NTR001 and chemotherapeutic agent cyclophosphamide on tumor volume in the mouse melanoma model.
Figure 6:
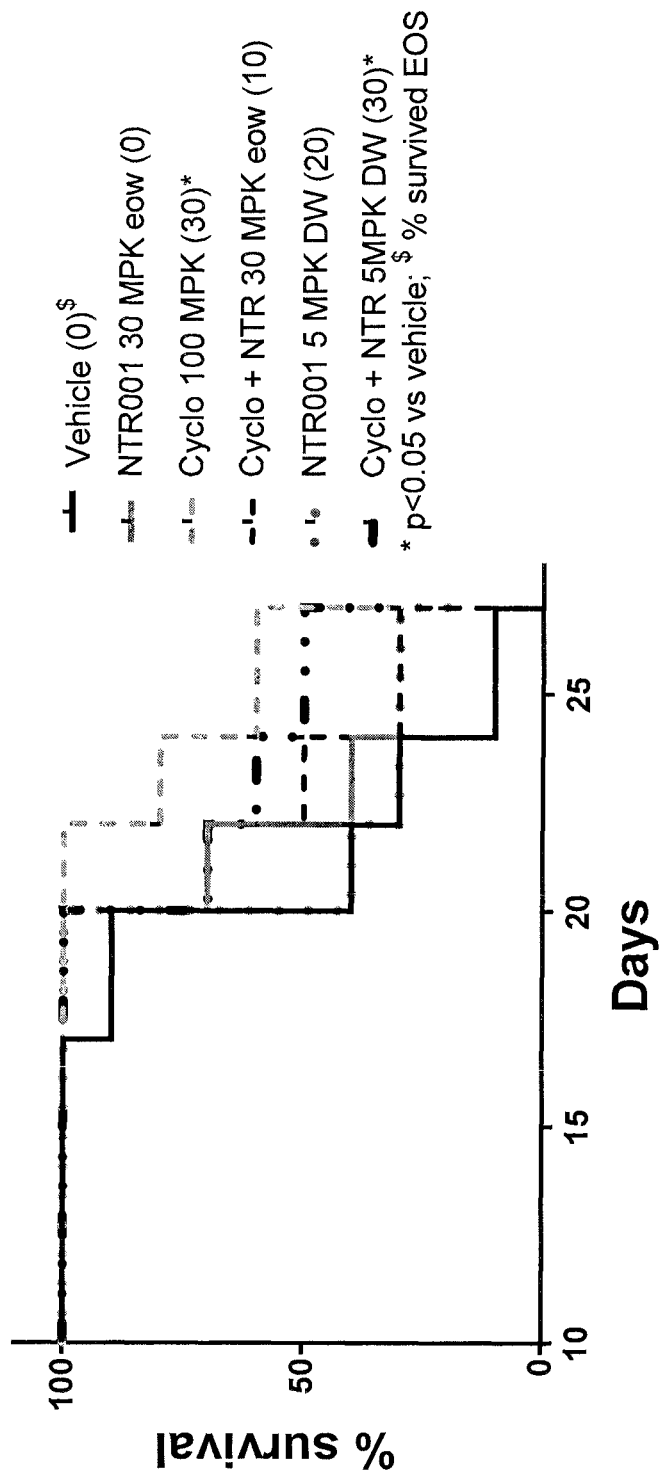
FIG. 6. Illustrates effect of PNP inhibitor NTR001 and chemotherapeutic agent cyclophosphamide on survival in the mouse melanoma model.

Results:

Treatment with NTR001 resulted in a significant decrease in tumor volume (FIG. 5). Treatment with NTR001 demonstrated 0-20% survival as single agent (FIG. 6). Cycicophosphamide and combination of cyclophosphamide with NTR001 at 5 mg/kg dose demonstrated 30% survival whereas there were no survivors in the vehicle treated group.

Conclusion:

PNP inhibitor NTR001 demonstrated significant efficacy in the syngeneic mouse melanoma model. Combinations of NTR001 with other anticancer and cancer immunotherapies such as checkpoint agonist, Yervoy, anti-PD1, etc. should be pursued. Treatment with alternate doses and dose schedule is also warranted.

EXAMPLE 4

Evaluation of Antibacterial Activity of PNPi in Mouse Model of L. Monocytogenes Infection Background:

In the past, antiviral and antibacterial research has focused mainly on viral and bacterial targets. Due to continued growth of drug resistant organisms the search for effective and differentiated antiviral and antibacterial therapies continues. Development of immune-potentiating agent is one of the strategies being pursued to identify new anti-infective agents. PNP inhibitors are novel small molecule immune-potentiating agents that may have some benefit in viral and bacterial infections.

Objective:

The objective of this study is to investigate whether PNP inhibitors NTR001 and NTR002 administered by oral and intraperitoneal routes demonstrate antibacterial effect in the mouse model of Listeria monocytogenes infection.

Method:

Balb/c mice are infected with $1\times10^6$ CFU of L. monocytogenes (ATCC Strain35152, hemolytic substrain) by intravenous route. The treatment of various groups is initiated −4 hr prior to infection except for Groups 3 and 7 for which treatment was initiated 2 days prior to infection and group 6 and 10 for which treatment was initiated 5 days prior to infection. Weight and survival are the end points of the study. Treatment arms were as follows:

TABLE 3

TREATMENT GROUPS

| Group | # mice | Treatment | Dose (mg/kg) | Route | Frequency |
|---|---|---|---|---|---|
| 1 | 5 | Vehicle | 10 ml/kg | PO | DAYS 0, 1, 2 |
| 2 | 10 | Vehicle | 10 ml/kg | PO | DAYS 0, 1, 2 |
| 3 | 10 | NTR001 | 30 | PO | DAYS −2, −1, 0, 1, 2 |
| 4 | 10 | NTR001 | 30 | PO | DAYS 0, 1, 2 |
| 5 | 10 | NTR001 | 30 | IP | DAYS 0, 1, 2 |
| 6 | 10 | NTR001 | 2 | DW | DAY − 5 thru end |
| 7 | 10 | NTR002 | 30 | PO | DAYS −2, −1, 0, 1, 2 |
| 8 | 10 | NTR002 | 30 | PO | DAYS 0, 1, 2 |
| 9 | 10 | NTR002 | 30 | IP | DAYS 0, 1, 2 |
| 10 | 10 | NTR002 | 2 | DW | DAY − 5 thru end |

PO = oral gavage;
IP = intraperitoneal injection;
DW = drinking water

Figure 7:
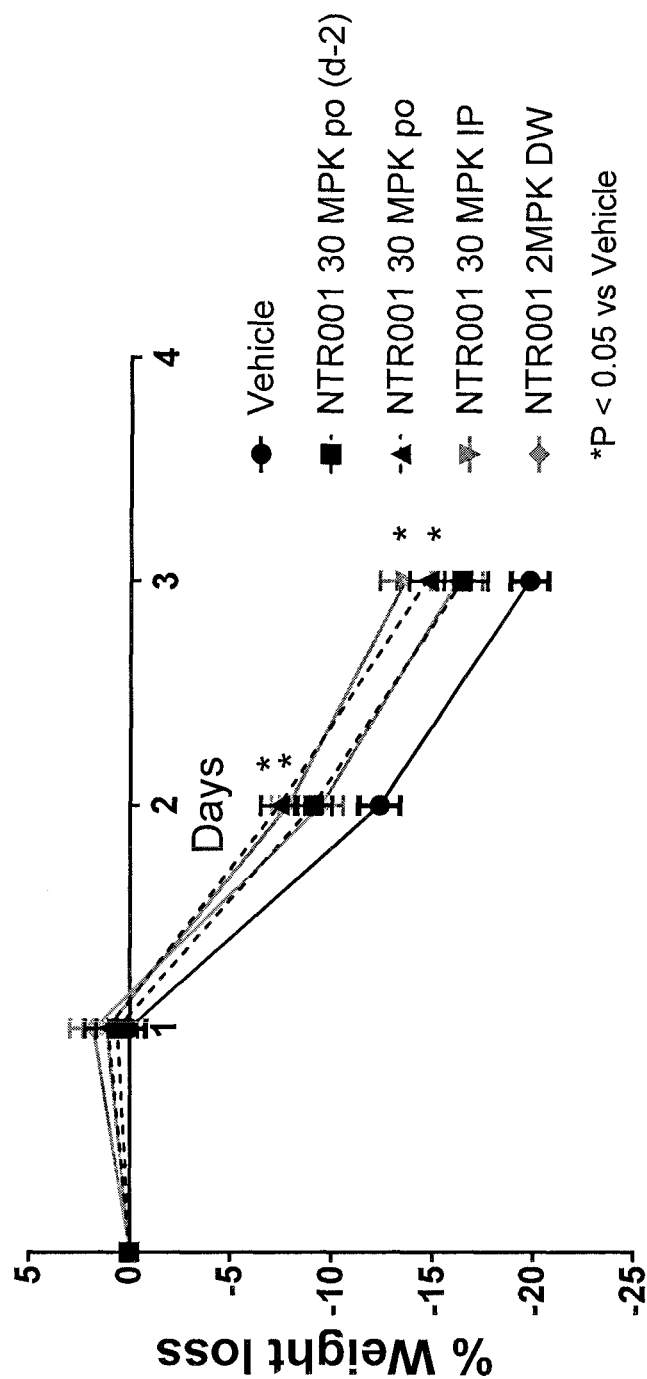
FIG. 7. Illustrates effect of PNP inhibitor NTR001 on weight loss in the mouse model of *L. Monocytogenes* infection.
Figure 8:
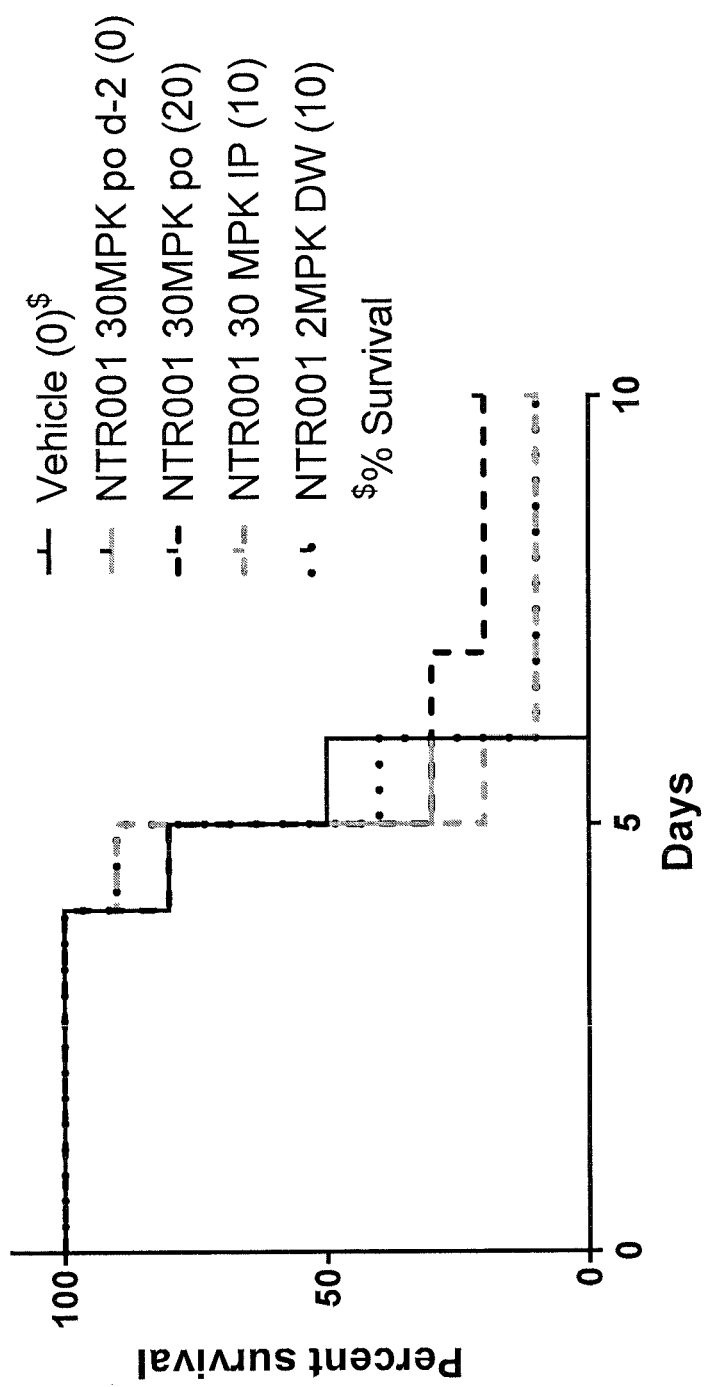
FIG. 8. Illustrates effect of PNP inhibitor NTR001 on survival in the mouse model of *L. Monocytogenes* infection.
Figure 9:
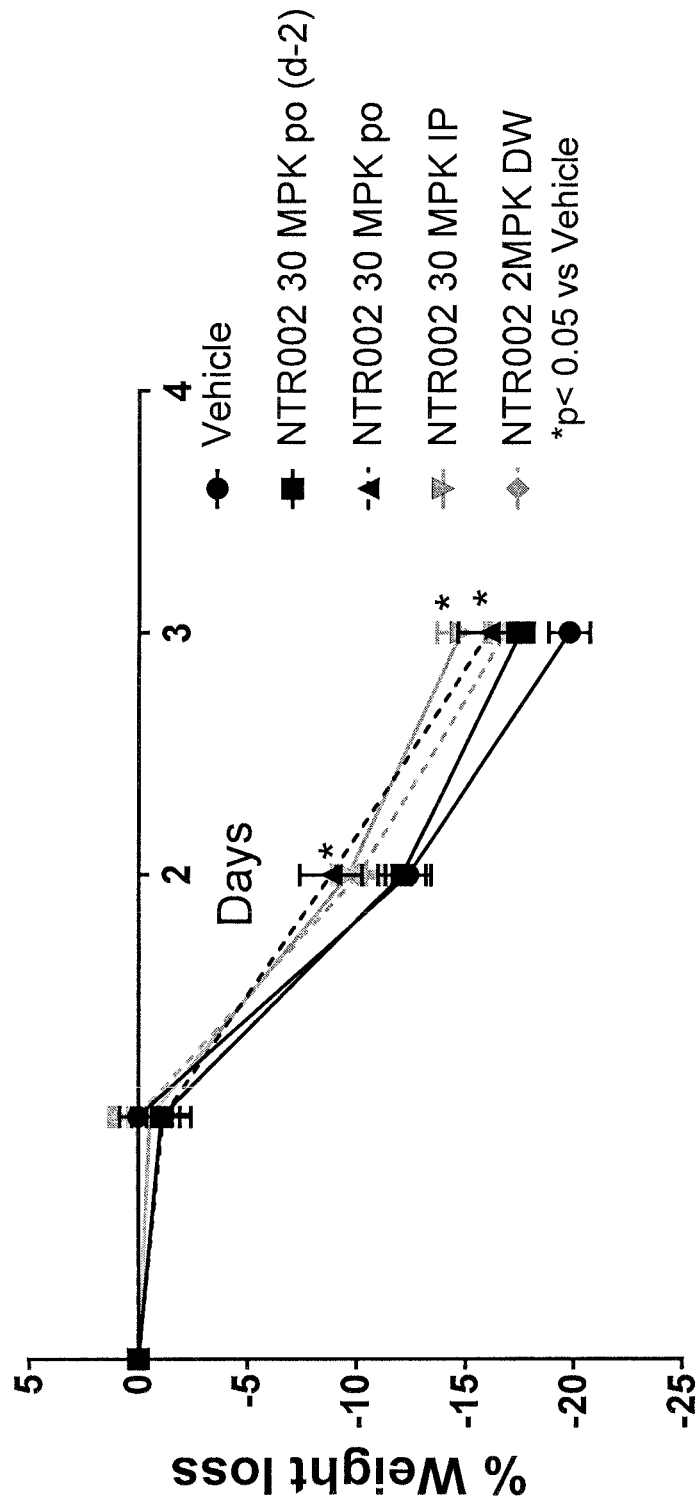
FIG. 9. Illustrates effect of PNP inhibitor NTR002 on weight loss in the mouse model of *L. Monocytogenes* infection.
Figure 10:
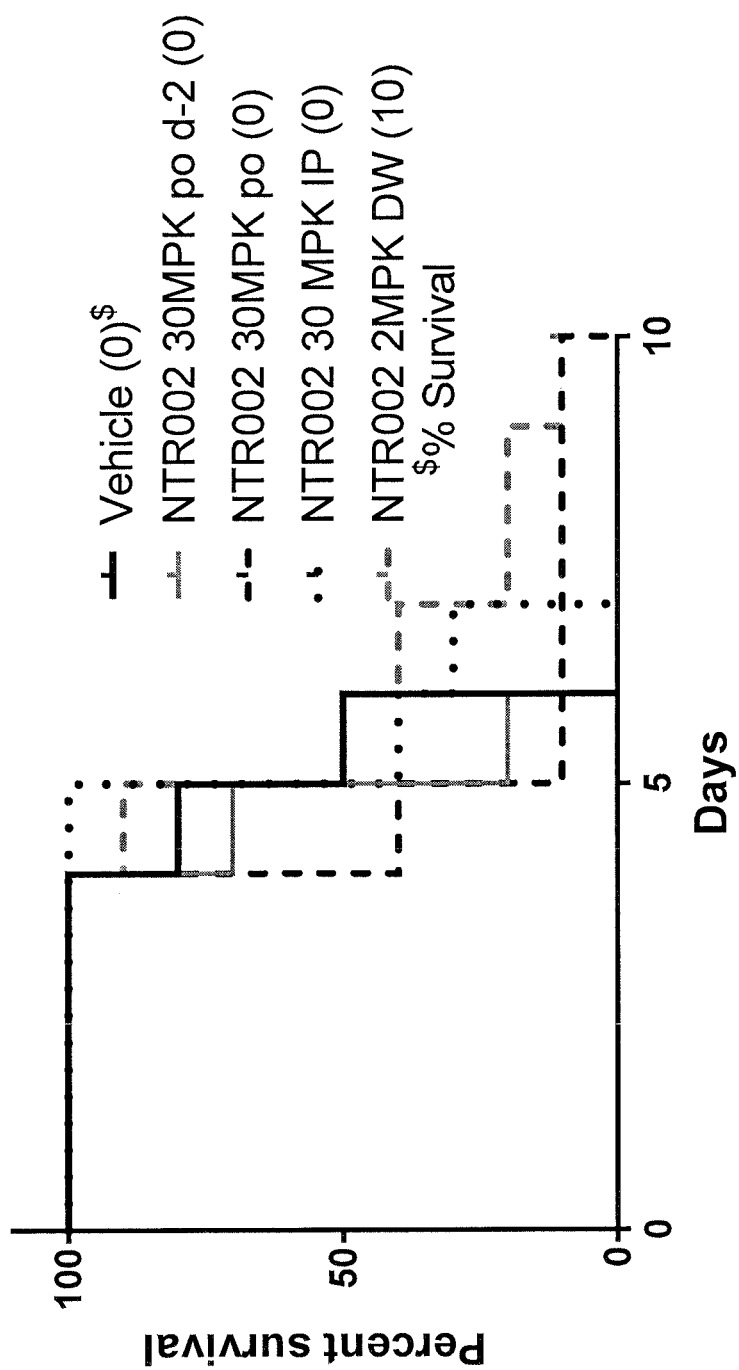
FIG. 10. Illustrates effect of PNP inhibitor NTR002 on survival in the mouse model of *L. Monocytogenes* infection.

Results:

Treatment with NTR001 and NTR002 resulted in significant decrease in weight loss (FIGS. 7 and 9) and protection of 10-20% of the animals (FIGS. 8 and 10).

Conclusion:

PNP inhibitors NTR001 and NTR002 demonstrated significant benefit in mouse model of *L. monocytogenes* infection. Combinations of NTR001 and NTR002 with other antibacterial agents should be pursued. Treatment with alternate doses and dose schedule is also warranted.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. It will be appreciated that the invention is in no way dependent upon particular results achieved in any specific example or with any specific embodiment. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims or from the description above is introduced into another claim. For example, any claim that is dependent on another claim can be modified to include one or more elements, limitations, clauses, or descriptive terms, found in any other claim that is dependent on the same base claim. Furthermore, where the claims recite a composition, it is to be understood that methods of using the composition for any of the purposes disclosed herein are included within the scope of the invention, unless otherwise indicated or unless it would be evident to one of ordinary skill in the art that a contradiction or inconsistency would arise. Methods can include a step of providing a subject suffering from a targeted disease or condition, or being at risk of developing a disease or condition, a step of diagnosing a subject as having a targeted disease or condition or as being at risk of a disease or condition, and/or a step of selecting a subject for which an inventive composition or method would be suitable.

Where elements are presented as lists, it is to be understood that each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Any particular embodiment, aspect, element, feature, etc., of the present invention, or any combination thereof, may be explicitly excluded from any one or more claims whether or not such exclusion is expressly recited herein. Applicants reserve the right to proviso out of the claims any specific agent or combination thereof, whether or not such agent or combination thereof, is recited herein.

The disclosures of all references cited herein are hereby incorporated into this specification in their entirety.

What is claimed:

1. A method for enhancing the potency of a vaccine, the method comprising: administering an amount of a purine nucleoside phosphorylase (PNP) inhibitor to a subject in conjunction with the vaccine, wherein said amount of the PNP inhibitor is effective to increase an amount of at least one endogenous adjuvant that activates toll-like receptors (TLR's).

2. The method according to claim 1, wherein the PNP inhibitor comprises a transition state analog of PNP having an in-vitro inhibitory constant Ki value of less than about $5 \times 10^{-6}$ M.

3. The method according to claim 2, wherein the in-vitro inhibitor constant Ki value is less than about $5 \times 10^{-8}$ M.

4. The method according to claim 1, wherein the PNP inhibitor comprises one or more compounds selected from Formula I (1,5-dihydro-7-[[(3R,4R)-3-hydroxy-4-(hydroxymethyl)pyrrolidin-1-yl]methyl]-4H-pyrrolo[3,2-d]pyrimidin-4-one), Formula II (7-[(2S,3S,4R,5R)-3,4-dihydroxy-5-(hydroxymethyl)-2-pyrrolidinyl]-1,5-dihydro-4H-pyrrolo[3,2-d]pyrimidin-4-one), and Formula III (7-[[(2R,3S)-1,3,4-trihydroxybutan-2-ylamino]methyl]-3H-pyrrolo[3,2-d]pyrimidin-4-one).

5. The method according to claim 4, wherein the PNP inhibitor is 1,5-dihydro-7-[[(3R,4R)-3-hydroxy-4-(hydroxymethyl)pyrrolidin-1-yl]methyl]-4H-pyrrolo[3,2-d]pyrimidin-4-one.

6. The method according to claim 4, wherein the PNP inhibitor is 7-[(2S,3S,4R,5R)-3,4-dihydroxy-5-(hydroxymethyl)-2-pyrrolidinyl]-1,5-dihydro-4H-pyrrolo[3,2-d]pyrimidin-4-one.

7. The method according to claim 1, further comprising administering at least one agent identified as an endogenous adjuvant in conjunction with administration of the PNP inhibitor.

8. The method according to claim 7, wherein the agent identified as an endogenous adjuvant is selected from the group consisting of guanosine, inosine, deoxyinosine, nicotinamide adenine dinucleotide, pro-drugs thereof, and combinations thereof.

9. The method according to claim 1 wherein "administering" is via an enteral or parenteral or topical route.

10. The method according to claim 1, wherein the vaccine comprises tetanus toxoid vaccine.

\* \* \* \* \*